United States Patent
Aqad et al.

(10) Patent No.: US 9,348,220 B2
(45) Date of Patent: May 24, 2016

(54) PHOTOACID GENERATORS AND PHOTORESISTS COMPRISING SAME

(75) Inventors: Emad Aqad, Shrewsbury, MA (US);
Mingqi Li, Marlborough, MA (US);
Cheng-Bai Xu, Southboro, MA (US);
Cong Liu, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/077,943

(22) Filed: Mar. 31, 2011

(65) Prior Publication Data

US 2011/0269070 A1 Nov. 3, 2011

Related U.S. Application Data

(60) Provisional application No. 61/319,700, filed on Mar. 31, 2010.

(51) Int. Cl.
| | | |
|---|---|---|
| G03F 7/004 | (2006.01) | |
| G03F 7/26 | (2006.01) | |
| C07C 303/32 | (2006.01) | |
| C07C 309/06 | (2006.01) | |
| C07C 309/07 | (2006.01) | |
| C07C 309/12 | (2006.01) | |
| C07C 309/19 | (2006.01) | |
| C07D 313/00 | (2006.01) | |
| C07D 315/00 | (2006.01) | |
| C07D 327/00 | (2006.01) | |
| G03F 7/038 | (2006.01) | |
| G03F 7/039 | (2006.01) | |

(52) U.S. Cl.
CPC ............ *G03F 7/0045* (2013.01); *C07C 303/32* (2013.01); *C07C 309/06* (2013.01); *C07C 309/07* (2013.01); *C07C 309/12* (2013.01); *C07C 309/19* (2013.01); *C07D 313/00* (2013.01); *C07D 315/00* (2013.01); *C07D 327/00* (2013.01); *G03F 7/0046* (2013.01); *G03F 7/0382* (2013.01); *G03F 7/0392* (2013.01); *G03F 7/0397* (2013.01); *G03F 7/0395* (2013.01)

(58) Field of Classification Search
CPC .. C07C 303/32; C07C 309/06; C07C 309/07; C07C 309/08; C07C 309/12; C07C 309/19; G03F 7/0045; G03F 7/0397; C07D 313/00; C07D 315/00; C07D 327/00

USPC ............ 430/270.1, 921, 922, 326; 562/100, 562/109, 113; 549/10, 12, 263, 268, 271
See application file for complete search history.

(56) References Cited

U.S. PATENT DOCUMENTS

| | | | |
|---|---|---|---|
| 7,527,912 B2* | 5/2009 | Ohsawa et al. ............. | 430/270.1 |
| 7,682,772 B2* | 3/2010 | Seshimo ............... | G03F 7/0045 |
| | | | 430/270.1 |
| 7,927,780 B2* | 4/2011 | Kawaue et al. ............. | 430/270.1 |
| 8,278,022 B2* | 10/2012 | Mimura et al. ............. | 430/270.1 |
| 8,609,891 B2* | 12/2013 | Bae ....................... | C07C 309/10 |
| | | | 430/270.1 |
| 2009/0162788 A1 | 6/2009 | Hada et al. | |
| 2009/0220890 A1* | 9/2009 | Hata ..................... | G03F 7/0045 |
| | | | 430/270.1 |
| 2010/0121077 A1 | 5/2010 | Seshimo et al. | |
| 2010/0203446 A1* | 8/2010 | Ichikawa et al. ............ | 430/270.1 |
| 2010/0248135 A1* | 9/2010 | Masuyama et al. ......... | 430/270.1 |
| 2010/0323294 A1 | 12/2010 | Li et al. | |

FOREIGN PATENT DOCUMENTS

EP 2141483 A1 6/2010

OTHER PUBLICATIONS

English Language Summary of Office Action issued in Counterpart Japanese Application No. 2011-076479, Dispatch Date Mar. 2, 2015 (4 Pages).
English Language Summary of Office Action issued in Counterpart Chinese Application (6 Pages).
English Summary of Japanese Publication No. 2010-052385, Published Sep. 22, 2011 (5 Pages).
English Summary of Japanese Application No. 2010-134445, Published Jun. 17, 2010 (2 Pages).
English Summary of Japanese Application No. 2006-162735, Published Jun. 22, 2006 (2 Pages).

* cited by examiner

*Primary Examiner* — John S Chu
(74) *Attorney, Agent, or Firm* — Mintz Levin Cohn Ferris Glovsky and Popeo, P.C.; Peter F. Corless

(57) ABSTRACT

New methods are provided for synthesis of photoacid generator compounds ("PAGs"), new photoacid generator compounds and photoresist compositions that comprise such PAG compounds. In a particular aspect, photoacid generators that comprise 1) a $SO_3^-$ moiety; 2) one or more fluorinated carbons; and 3) one or more of the fluorinated carbons either directly or indirectly substituted by an ester keto group.

13 Claims, No Drawings

PHOTOACID GENERATORS AND PHOTORESISTS COMPRISING SAME

This application claims the benefit of priority under 35 U.S.C. §119(e) to U.S. Provisional Application No. 61/319,700, filed Mar. 31, 2010, the entire contents of which application are incorporated herein by reference.

This invention relates to methods for synthesis of photoacid generator compounds ("PAGs"), new photoacid generator compounds and photoresist compositions that comprise such PAG compounds. In particular, the invention relates to photoacid generators that comprise 1) a $SO_3^-$ moiety; 2) one or more fluorinated carbons; and 3) one or more of the fluorinated carbons either directly or indirectly substituted by an ester keto group.

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See, e.g., U.S. Pat. Nos. 6,664,022 and 6,849,374.

In one aspect, we now provide novel photoacid generator compounds (PAGs) that comprise a sulfonic acid ($SO_3^-$) component for use in either positive-acting or negative-acting photoresist compositions.

Preferred PAGs of the invention comprise 1) a $SO_3^-$ moiety, 2) one or more fluorinated carbons (e.g. one or more —$CF_2$—, —CHF—), and 3) one of more of the fluorinated carbons either directly or indirectly substituted by an ester keto group e.g. —C(=O)OR where R is a hydrogen or preferably non-preferably substituent. A fluorinated carbon is indirectly substituted by an ester keto group e.g. —C(=O)OR where non-fluorinated carbons and/or hetero atoms are interposed between the fluorinated carbon and the ester keto group, and a f fluorinated carbon is directly substituted by an ester keto group e.g. —C(=O)OR where no non-fluorinated carbons and/or hetero atoms are interposed between the fluorinated carbon and the ester keto group. In many aspects, it is preferred that a fluorinated carbon is indirectly substituted by an ester keto group. Also preferred are PAGs that comprise one or more fluoinrated carbons (including difluorocarbons) (e.g. —$CHF_2$—, —$CF_2$—), particularly where a —$CF_2$— moiety is directly bonded to a $SO_3^-$ moiety i.e. —$CF_2$—$SO_3^-$.

Particularly preferred photoacid generator compounds of the invention may comprise a structure of the following formula (I):

$$RO(C=O)(CXY)_p(CF_2)_nSO_3^-M^+ \quad (I)$$

wherein R is hydrogen or preferably non-hydrogen substituent such as optionally substituted alkyl including optionally substituted $C_{1-30}$alkyl, optionally substituted including $C_{3-30}$ cycloalkyl, optionally substituted alkoxy including optionally substituted $C_{1-30}$alkoxy, optionally substituted carbocyclic including C6-30 carbocyclic group, optionally substituted heteroalicyclic including $C_{3-30}$ heteroalicyclic that contains 1, 2 or 3 N, O and/or S ring atoms, and the like;

X and Y are each independently hydrogen or a non-hydrogen substituent such as halo (particularly fluoro), cyano, nitro, or a non-hydrogen substituent as set forth above for R;

p is 0 or a positive integer, and preferably p is 1, 2 or 3;

$M^+$ is a positive integer and preferably is 1, 2 or 3, more preferably 1 or 2;

M+ is a counter ion, and preferably is an organic onium salt component, such as a sulfonium or iodonium cation component, particularly a trisubstituted sulfonim caton or a disubstituted iodonium cation.

In certain aspects, especially preferred photoacid generator compounds of the invention may comprise a structure of the following formula (II):

$$RO(C=O)(CH_2)_p(CF_2)_nSO_3^-M^+ \quad (II)$$

wherein R, p, n and M+ are the same as specified for formula I above.

In certain aspects, preferred R groups of formulae (I) and/or (II) above include carbon alicyclic such as optionally substituted adamantyl e.g. adamantyl, hydroxyadamantyl, cyanoadamantyl; and heteroalicylic groups such as cyclic lactone; and the like.

In a preferred aspect, PAGs of the invention that comprise a sulfonic anion component also contain a chain that has at least four saturated non-cyclic atoms (typically carbon or hetero N, O or S, more typically carbon or oxygen, even more typically each linked member of the saturated chain is carbon) between (i) a sulfonic moiety ($SO_3^-$) and (ii) (a) a non-saturated moiety (e.g. phenyl or other carboxyclic aryl), keto (carbonyl), ester, and the like or (b) an alicyclic group such as cyclohexyl, and the like. Exemplary anion components may include those of the following formula: $RO(C=O)(CH_2)_n(CF_2)_mSO_3^-$ where the sum of n and m is at least four, and R is hydrogen or non-hydrogen as specified above for formulae (I) and (II)).

Preferably, PAGs of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Preferred im wavelengths of photoresists of the invention include sub-300 nm wavelengths e.g. 248 nm, and sub-200 nm wavelengths e.g. 193 nm and EUV.

Particularly preferred photoresists of the invention contain an imaging-effective amount of one or more PAGs as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups;

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. No. 5,843,624 incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083.

Resists of the invention also may comprise a mixture of distinct PAGs, typically a mixture of 2 or 3 different PAGs, more typically a mixture that consists of a total of 2 distinct PAGs.

The invention also provide methods for forming relief images of the photoresists of the invention, including methods for forming highly resolved patterned photoresist images (e.g. a patterned line having essentially vertical sidewalls) of sub-quarter micron dimensions or less, such as sub-0.2 or sub-0.1 micron dimensions.

The invention further provides articles of manufacture comprising substrates such as a microelectronic wafer or a flat panel display substrate having coated thereon the photoresists and relief images of the invention. Other aspects of the invention are disclosed infra.

As discussed, particularly preferred photoacid generator compounds of the invention may comprise a structure of either or both of the following formulae (I) or (II):

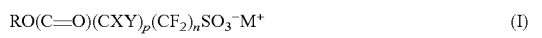

RO(C=O)(CXY)$_p$(CF$_2$)$_n$SO$_3^-$M$^+$      (I)

RO(C=O)(CH$_2$)$_p$(CF$_2$)$_n$SO$_3^-$M$^+$      (II)

wherein R, X, Y, p, n and M+ are the same as specified above for formula (I) and (II).

In certain preferred aspects, the substituent R may comprise adamantane or substituted adamantane structure presented by the formula (III):

wherein in formulae (III) X is H or OH.

In additional preferred aspects, R may contain a bi- or multi-cyclic (e.g. 2, 3, 4, 5, or 6 covalently linked or fused rings) structure that comprises a lactone functionality, e.g. as may be represented by the following formulae (IV) and (V):

wherein each of formulae (IV) and (V) X is a methylene group (—CH$_2$—) or oxygen atom (—O—).

In yet additional preferred aspects, R may contain a bi- or multi-cyclic (e.g. 2, 3, 4, 5, or 6 covalently linked or fused rings) structure that comprise a sulfone functionality (particularly as a ring-member), e.g. as may be represented by the following formula (VI):

wherein in formula (VI) X is a methylene group (—CH2—) or oxygen atom (—O—).

In still additional preferred aspects, R may be also a hydrocarbon that has a steroid structure. As referred to herein, a steroid structure designates compounds of the structure having three six-membered rings and one five-membered ring fused together as represented by the general formula (VII):

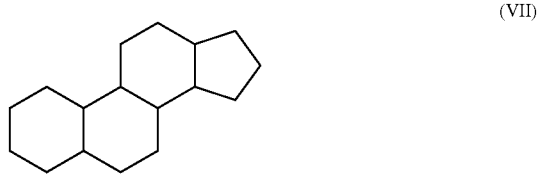

Generally preferred onium salt components of PAGs of the invention include sulfonium and iodonium salt photoacid generators, such as those compounds disclosed in published European application 0 708 368 A1. Such salts include those represented by the following formulae (VIII) and (IX):

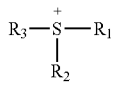
(VIII)

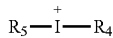
(IX)

wherein in formulae (VIII) and (IX) $R_1$ to $R_5$ each independently represents alkyl group or a substituted or unsubstituted 1 aryl group. A preferred example of the aryl group includes a $C_{6-14}$ monocyclic or a condensed ring aryl group. Preferred examples of the substituent on the aryl group include an alkyl group, a haloalkyl group, a cycloalkyl group, an aryl group, an alkoxy group, a nitro group, a carboxyl group, an alkoxycarbonyl group, a hydroxyl group, mercapto group, and a halogen atom.

Particularly preferred anion (sulfonate) compounds of the invention include those compounds that comprise one of the following structures:

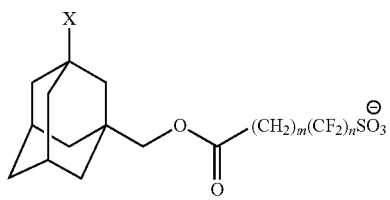

n = 1, 2
m = 1,2,3
X = H, OH

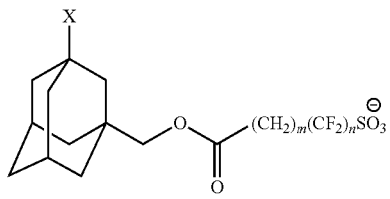

n = 1, 2
m = 1,2,3
X = H, OH

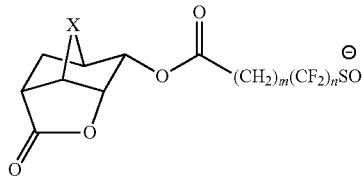

n = 1, 2
m = 1,2,3
X = CH2, O

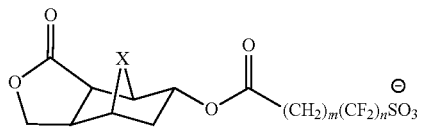

n = 1, 2
m = 1,2,3
X = CH2, O

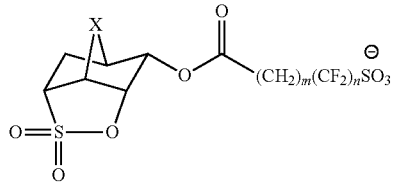

n = 1, 2
m = 1,2,3
X = CH2, O

Particularly preferred anion (sulfonate) compounds of the invention include the following compounds:

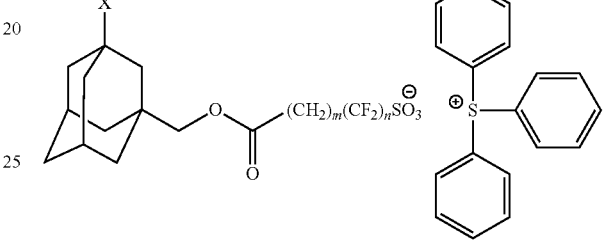

n = 1, 2
m = 1,2,3
X = H, OH

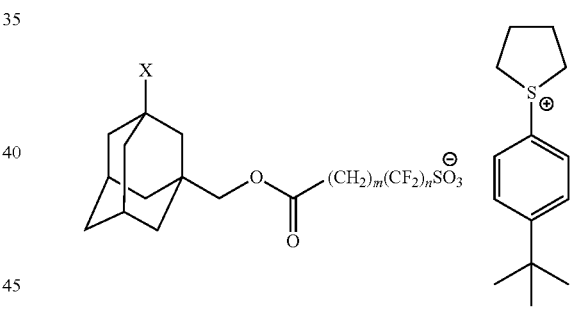

n = 1, 2
m = 1,2,3
X = H, OH

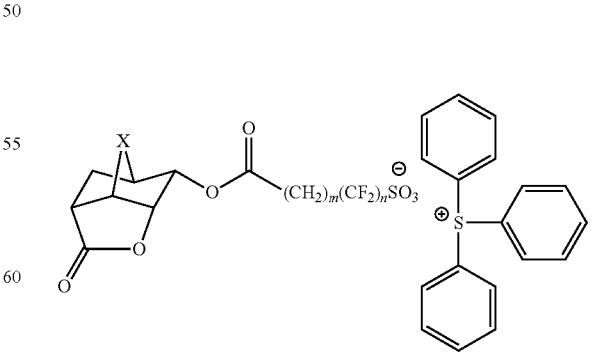

n = 1, 2
m = 1,2,3
X = CH2, O

-continued

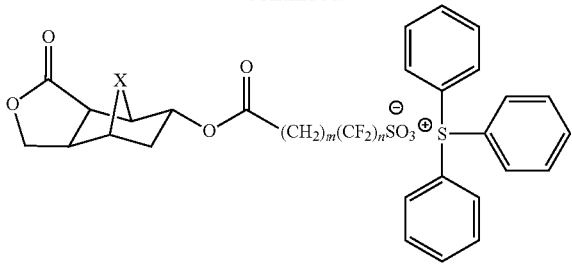

n = 1, 2
m = 1,2,3
X = CH2, O

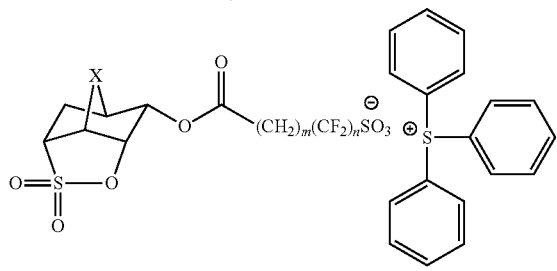

n = 1, 2
m = 1,2,3
X = CH2, O

As stated herein above, various substituent groups of PAGs of the invention may be optionally substituted. Substituted moieties are suitably substituted at one or more available positions by, e.g., halogen such as F, Cl Br and/or I, nitro, cyano, sulfono, alkyl including $C_{1-16}$ alkyl with $C_{1-8}$ alkyl being preferred, haloalkyl such as fluoroalkyl (e.g. trifluoromethyl) and perhaloalkyl such as perfluoro$C_{1-4}$ alkyl, alkoxy including $C_{1-16}$ alkoxy having one or more oxygen linkages with $C_{1-8}$ alkoxy being preferred, alkenyl including $C_{2-12}$ alkenyl with $C_{2-8}$ alkenyl being preferred, alkenyl including $C_{2-12}$ alkenyl with $C_{2-8}$ alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthracenyl and naphthyl.

As used herein, alkoxy groups of PAG compounds of the invention have one or more oxygen linkages, typically 1 to about 5 or 6 oxygen linkages. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S). Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, and benzothiazole.

Photoacid generator compounds of the invention may be readily produced. Exemplary snyhteses are set forth in the examples which follow. For instance, a fluorinated acid (e.g. HOC(=O)(CH2)$_p$(CF2)$_m$Br (where p is 0 to 10, and m is 1 to 10) can be esterified (to provide an R group as defined above for formulae I and II, e.g. to provide a compound HOC(=O)(CH2)$_p$(CF2)$_m$Br) followed by oxidation to form the sulfonic acid which may include treatment with an oxidizing agent such as hydrogen peroxide and use of a catalyst NaWO$_4$.2H$_2$O.

As discussed above, PAGs of the invention are useful as the radiation sensitive component in photoresist compositions, including both positive-acting and negative-acting chemically amplified resist compositions.

The photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution.

Preferably, a photoacid generator compound of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

PAGs of the invention also are preferably used with polymers that contain one or more photoacid-labile groups and that are substantially, essentially or completely free of phenyl or other aromatic groups. Such photoresist compositions are particularly useful for imaging with sub-200 nm radiation such as 193 nm radiation.

For example, preferred polymers contain less than about 5 mole percent aromatic groups, more preferably less than about 1 or 2 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged with such short wavelength radiation.

Suitable polymers that are substantially or completely free of aromatic groups and may be formulated with a PAG of the invention to provide a photoresist for sub-200 nm imaging are disclosed in European application EP930542A1 of the Shipley Company.

Suitable polymers that are substantially or completely free of aromatic groups suitably contain acrylate units such as photoacid-labile acrylate units as may be provided by polymerization of methyladamanatylacrylate, methyladamanylmethacrylate, ethylfencylacrylate, ethylfencylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride; and the like.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

Photoresists of the invention also may contain other materials. For example, other optional additives include actinic and contrast dyes, anti-striation agents, plasticizers, speed enhancers, sensitizers, etc. Such optional additives typically will be present in minor concentration in a photoresist composition except for fillers and dyes which may be present in relatively large concentrations such as, e.g., in amounts of from 5 to 30 percent by weight of the total weight of a resist's dry components.

A preferred optional additive of resists of the invention is an added base, particularly tetrabutylammonium hydroxide (TBAH), which can enhance resolution of a developed resist relief image. The added base is suitably used in relatively small amounts, e.g. about 1 to 10 percent by weight relative to the PAG, more typically 1 to about 5 weight percent. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; propionates, particularly methyl propionate and ethyl propionate; a Cellosolve ester such as methyl Cellosolve acetate; an aromatic hydrocarbon such toluene or xylene; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 1 to 300 mJ/cm². As discussed above, preferred exposure wavelengths include sub-200 nm such as 193 nm. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The following non-limiting example is illustrative of the invention.

EXAMPLE 1

PAG Synthesis

Synthesis of TPS 3OH-AdTFBuS

The four steps synthesis of TPS 3OH-AdTFBuS is described in the following Scheme 1 and below.

Scheme 1

Step 1:

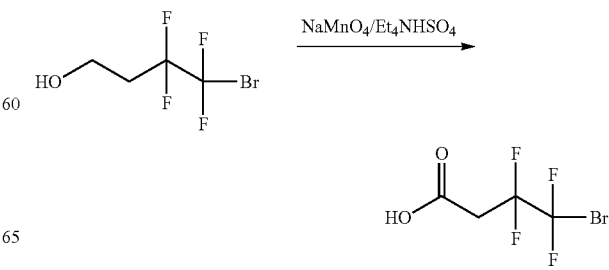

Step 2:

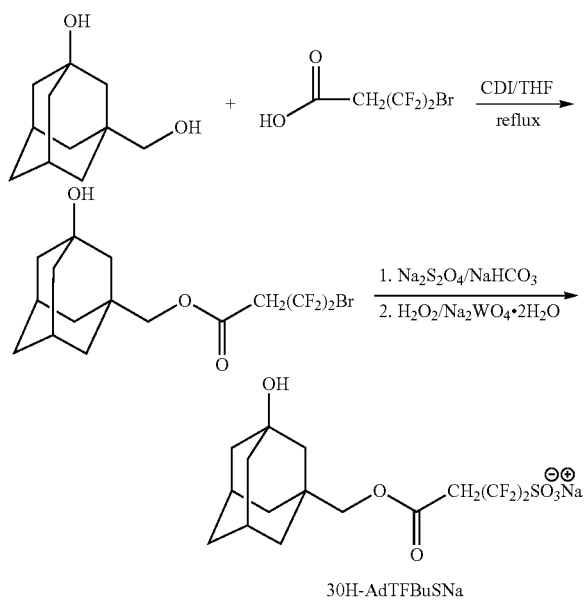

3OH-AdTFBuSNa

Step 3:

TPS 3OH-AdTFBuS

1. Synthesis of 4-Bromo-3,3,4,4-tetrafluorobutyric acid:

To a mixture of 4-bromo-3,3,4,4-tetrafluorobutanol (30 g, 133.35 mmol), tetraethylammonium hydrogensulfate (20 mg) in 150 ml of water is added dropwise a solution of sodium permanganate (26.5 g) in 100 ml of water. After complete addition of the permanganate solution the reaction mixture is stirred at 65 C for 4 h. The reaction mixture is cooled to room temperature and the precipitate is filtered. The filtrate (aqueous solution) is extracted twice with methyl t-butyl ether. The aqueous solution is acidified with concentrated sulfuric acid until pH=1. The mixture is transferred to a separatory funnel, a colorless lower layer was separated (first fraction of pure product), the aqueous phase is extracted twice with 100 ml of methyl t-butyl ether. The combined methyl t-butyl ether solution is dried over magnesium sulfate, filtered and methyl t-butyl ether is completely removed under reduced pressure to produce a second fraction of pure product. Overall yield=27 g (85%).

2. Synthesis of 3OH-AdTFBuSNa:

To a 250 ml flask were added 15 g of the 4-Bromo-3,3,4,4-tetrafluorobutyric acid (63.1 mmol) and 150 ml of anhydrous tetrahydrofurane (THF) under a nitrogen ($N_2$) sweep. To this mixture is added 1',1'-carbonyldiimidazole (CDI, 11.2 g) in portions over a 30 min period. After the addition is completed, the reaction is held at room temp for 3 hrs. The mixture is heated to reflux and then 3-hydroxymethyl-adamantan-1-ol (11.5 g) is added over a 5 min period. The mixture is kept at reflux for additional 15 h. The reaction is cooled to 25 C, added to a separatory funnel then 4-5 volumes of water are added. The bottom layer is collected and the top layer is washed with 300 ml of ethyl acetate. The amber oil and the ethyl acetate solution are combined then washed with 4×200 ml deionized water. The pH of the water washes goes from ~9 to ~6.5. The ethyl acetate is dried over $MgSO_4$ and removed under reduced pressure to produce an oil, which can be used without further purification.

The above oil is combined with 26.6 g sodium thiosufite, 19.3 g sodium bicarbonate, 150 ml of acetonitrile and 150 ml of deionized water. This mixture is held overnight (16 hrs) at 60 C. The mixture is cooled to room temp. The acetonitrile layer is collected and placed in another 500 ml flask and 100 ml of deionized water is added followed by 13 g 30% hydrogen peroxide and 60 mg of the catalyst ($NaWO_4.2H_2O$). The solution is stirred for 2-3 hrs at room temp. After the reaction is complete, 13 g of sodium bisulfate is added slowly to neutralize any residual $H_2O_2$. To the pale yellow one phase system is added 30 g of sodium chloride resulting in a two phase system. The upper layer is collected, dried over $MgSO_4$ and then slowly added to 1.4 L of stirred methyl t-butylether to yield the product 3OH-AdTFBSuNa. The product is filtered and dried and used in step 3.

3. Synthesis of TPS 3OH-AdTFBuS:

A mixture made of 10 g of 3OH-AdTFBSuNa, 8 g of triphenyl sulfonium bromide in 50 ml methylene chloride and 50 ml of deionized water is stirred at room temperature for 18 hours. The layers are separated and the bottom organic layer is washed with 10×500 ml of deionized water. The methylene chloride is dried over $MgSO_4$ then reduced in volume by about 40%. The methylene chloride solution is slowly added to 10 L of Methyl t-butyl ether to produce the product 3OH-AdTFBSu which can be filtered and dried.

EXAMPLE 2

Photoresist Preparation and Lithographic Processing

A photoresist of the invention is prepared by mixing the following components with amounts expressed as weight percent based on total weight of the resist compositions:

| Resist components | Amount (wt. %) |
| --- | --- |
| Resin binder | 15 |
| Photoacid generator | 4 |
| Ethyl lactate | 81 |

The resin binder is a terpolymer (2-methyl-2-adamantyl methacrylate/beta-hydroxy-gamma-butyrolactone methacrylate/cyano-norbornyl methacrylate. The photoacid generator is the compound TPS DHC-TFBS, as prepared in Example 1 above. Those resin and PAG components are admixed in the ethyl lactate solvent.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26 N aqueous tetrabutylammonium hydroxide solution to develop the imaged resist layer.

What is claimed is:

1. A photoacid generator compound that comprises a structure of the following formula (I):

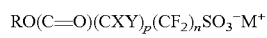

wherein R is hydrogen or non-hydrogen substituent;

X and Y are each independently hydrogen or a non-hydrogen substituent;

p is a positive integer;

n is a positive integer;

M+ is a counter ion.

2. A photoacid generator compound of claim 1 that comprises a structure of the following formula (II):

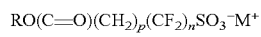

3. A photoacid generator of claim 1 wherein the sum of p and n is at least four.

4. A photoacid generator of claim 1 wherein R is a carbon alicylic or heteroalicylic group.

5. A photoacid generator of claim 1 wherein M+ is a sulfonium or iodonium cation.

6. A photoacid generator compound of claim 1 wherein the photoacid generator compound comprises a structure selected from the following:

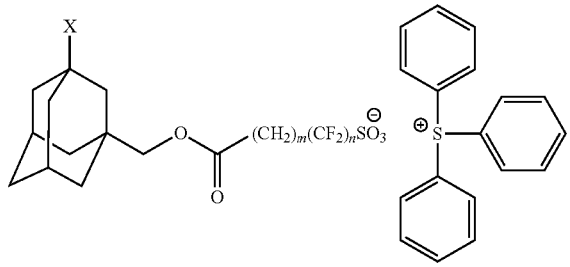

n = 1, 2
m = 1,2,3
X = H, OH

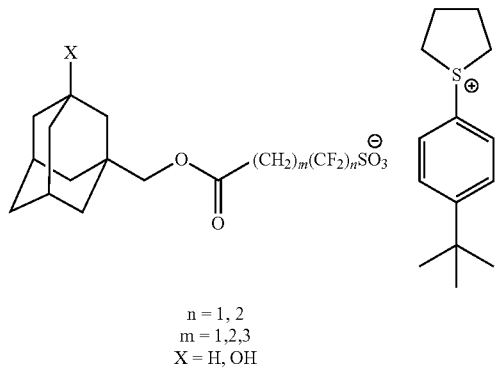

n = 1, 2
m = 1,2,3
X = H, OH

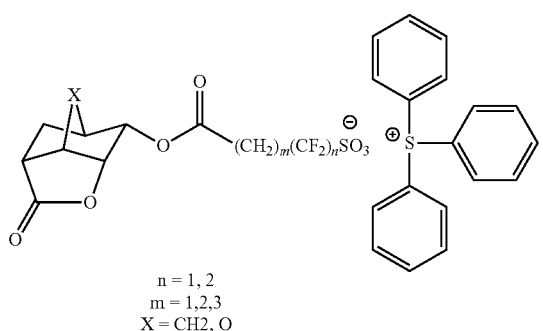

n = 1, 2
m = 1,2,3
X = CH2, O

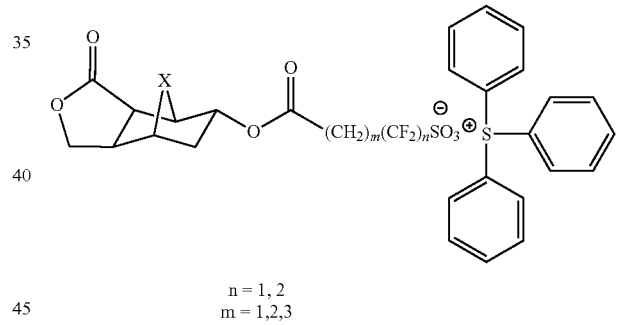

n = 1, 2
m = 1,2,3
X = CH2, O

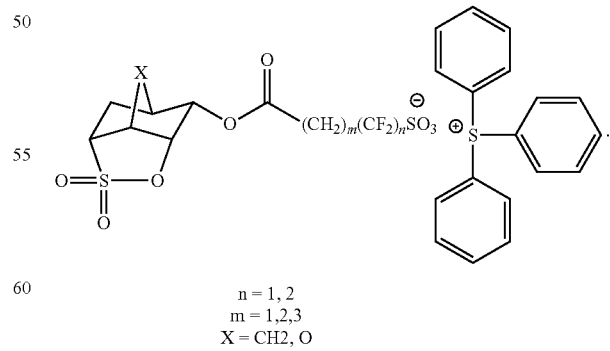

n = 1, 2
m = 1,2,3
X = CH2, O

7. A photoacid generator compound of claim 1 wherein the photoacid generator compound comprises a structure selected from the following:

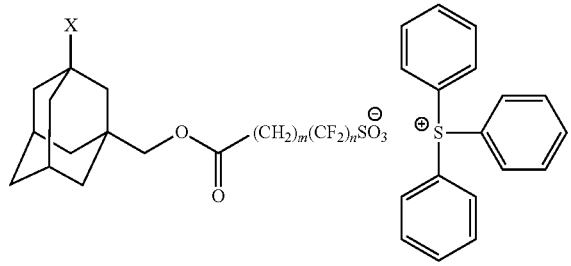

n = 1, 2
m = 1,2,3
X = H, OH

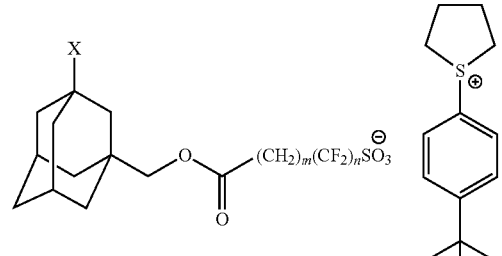

n = 1, 2
m = 1,2,3
X = H, OH

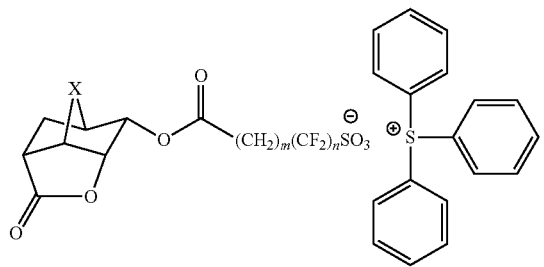

n = 1, 2
m = 1,2,3
X = CH2, O

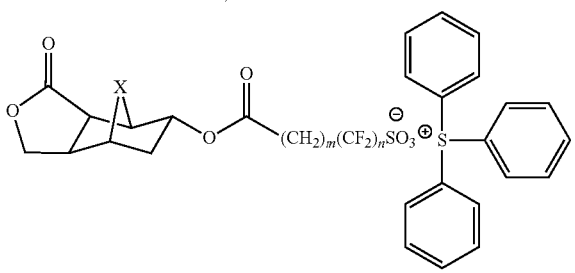

n = 1, 2
m = 1,2,3
X = CH2, O

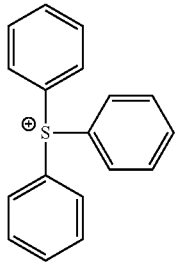

n = 1, 2
m = 1,2,3
X = CH2, O

8. A photoresist composition comprising a resin component and a photoacid generator compound of claim 6.

9. A method for forming a photoresist relief image comprising:

a) applying a coating layer of a photoresist composition of claim 8 on a substrate;

b) exposing the photoresist coating layer to patterned activating radiation and developing the exposed photoresist layer to provide a relief image.

10. A photoresist composition comprising a resin component and a photoacid generator compound of claim 7.

11. A method for forming a photoresist relief image comprising:

a) applying a coating layer of a photoresist composition of claim 10 on a substrate;

b) exposing the photoresist coating layer to patterned activating radiation and developing the exposed photoresist layer to provide a relief image.

12. A photoresist composition comprising a resin component and a photoacid generator compound of claim 1.

13. A method for forming a photoresist relief image comprising:

a) applying a coating layer of a photoresist composition of claim 12 on a substrate;

b) exposing the photoresist coating layer to patterned activating radiation and developing the exposed photoresist layer to provide a relief image.

\* \* \* \* \*